United States Patent [19]

Fujimori et al.

[11] Patent Number: 5,234,928
[45] Date of Patent: Aug. 10, 1993

[54] QUINAZOLINE-3-ALKANOIC ACID DERIVATIVES, THEIR SALTS AND THEIR PREPARATION PROCESSES

[75] Inventors: Shizuyoshi Fujimori, Marubayashi; Michiro Ohnota, Nogi; Yoshihiro Hirata, Omiya; Koji Murakami, Nogi, all of Japan

[73] Assignee: Kyorin Pharmaceutical Co., Ltd., Tokyo, Japan

[21] Appl. No.: 721,610
[22] PCT Filed: Dec. 10, 1990
[86] PCT No.: PCT/JP90/01600
  § 371 Date: Jul. 17, 1991
  § 102(e) Date: Jul. 17, 1991
[87] PCT Pub. No.: WO91/09024
  PCT Pub. Date: Jun. 27, 1991

[30] Foreign Application Priority Data

Dec. 11, 1989 [JP] Japan ................... 1-321097

[51] Int. Cl.[5] .................. A61K 31/505; C07D 239/96
[52] U.S. Cl. ........................... 514/259; 544/285
[58] Field of Search ............ 544/285; 514/259

[56] References Cited

U.S. PATENT DOCUMENTS 4,556,739 12/1985 Kanojia et al. ............... 564/443
4,931,440 6/1990 Nakashima et al. .......... 514/259
4,957,923 9/1990 Nakashima et al. .......... 514/259

FOREIGN PATENT DOCUMENTS 277687 4/1990 Fed. Rep. of Germany.
57-95966 6/1982 Japan.

OTHER PUBLICATIONS

Chemical Abstracts 115 232282 (1991).
Chemical Abstracts 114 247224 (1991).
Chemical Abstracts 110 154257 (1988).
Chemical Abstracts 110 88390 (1988).
Chemical Abstracts 109 93043 (1987).
Chemical Abstracts 108 6052 (1987).
Chemical Abstracts 102 89620 (1984).

(List continued on next page.)

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

The present invention relates to quinazoline-3-alkanoic acid derivatives having both an inhibitory effect on platelet aggregation and a hindering effect on aldose reductase together, represented by a general formula [I]

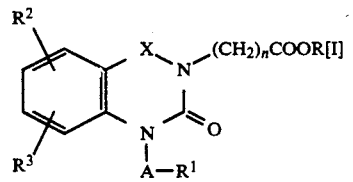

[wherein R is hydrogen or a protecting group for carboxyl group, $R^1$ is a lower alkyl group, alkenyl group, alkinyl group, lower alkoxy group, lower alkylthio group, halogen, phenyl group (this phenyl group may be substituted by one to three of lower alkyls, lower alkoxys, halogens, trifluoromethyls, carboxyethylenes or ethoxycarbonylethylenes, naphthyl group, heterocycle (this heterocycle may be substituted by one to three of lower alkyls), cycloalkyl group or benzoyl group (this benzoyl group may be substituted by lower alkyl or halogen), $R^2$ and $R^3$ are identically or differently hydrogens, halogens, lower alkyl groups, lower alkoxy groups, aralkyl groups which may be substituted, nitro groups, imidazolyl groups, imidazolylmethyl groups or

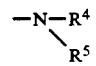

($R^4$ and $R^5$ indicate identically or differently hydrogens or lower alkyl groups, or connected with each other to make five- or six-membered heterocycles which may contain other hetero atom, X is carbonyl, thiocarbonyl or methylene group (this methylene group may be substituted by lower alkyl group), A is lower alkylene or lower alkenylene, and n indicates an integer of 1 to 3], their salts, their preparation processes and medicinal drugs containing them.

3 Claims, No Drawings

OTHER PUBLICATIONS

Chemical Abstracts 97 72322 (1982).
Chemical Abstracts: 96: 162734 (1980).
Chemical Abstracts 95: 97718 (1981).
Akgun et al. Journal of Pharmaceutical Sciences 77(9) (Sep. 1988) pp. 735–739.
Malamas et al., Journal of Medicinal Chemistry 34(4) (1991) pp. 1492–1503.

Chemical Abstracts, 168619k, vol. 107, 1987, p. 46, A. R. El Nasser Ossman, et al.,: "Synthesis and Anticonvulsant Activity of Some New 2,4-(1H,3H)-Quinazoline Derivatives".

European Journal of Medicinal Chemistry, vol. 25, 1990, pp. 121–125, E. Billon, et al.,: "Aldose Reductase Inhibition by 2,4-Oxo and Thioxo Derivatives of 1,2,3,4-Tetrahydroquinazoline".

QUINAZOLINE-3-ALKANOIC ACID DERIVATIVES, THEIR SALTS AND THEIR PREPARATION PROCESSES

TECHNICAL FIELD

The present invention relates to novel quinazoline-3-alkanoic acid derivatives having inhibitory effects on platelet aggregation and aldose reductase activity, their salts, their preparation processes and medicinal drugs containing them.

BACKGROUND TECHNIQUES

Recently, it has been made clear that the platelets and the arachidonic acid metabolites play an important role for the origin of thrombotic diseases such as cardiac infarction and the prevention therefrom, and the development of useful drugs therefor such as inhibitory agent of platelet aggregation is expected. On the other hand, with the diabetic neuropathy and complications of diabetes mellitus, the participation of aldose reductase has been made clear, thus the inhibition of the activity of aldose reductase will be connected with the therapy and the prevention of complications originating from diabetes mellitus.

Compounds having inhibitory effect on platelet aggregation or compounds having inhibitory effect on aldose reductase are widely searched separately. For example, the fact that quinazoline-1-alkanoic acid derivatives have the inhibitory effect on aldose reductase is disclosed in Japanese Unexamined Patent Publication No. Sho 62-96476, No. Hei 1-125322 and No. Hei 1-131164, but these compounds have no inhibitory effect on platelet aggregation. The quinazoline-3-alkanoic acid derivatives of the invention are novel compounds, and any prior art to allow to presume that the compounds of the invention have both the inhibitory effect on platelet aggregation and the inhibitory effect on aldose reductase cannot be found.

The purpose of the invention is to provide useful compounds as medicinal drugs having excellent inhibitory effect on aldose reductase together with strong inhibitory effect on platelet aggregation.

DISCLOSURE OF THE INVENTION

As a result of diligent studies to solve such problem, the inventors have found that quinazoline-3-alkanoic acid derivatives represented by a general formula [I]

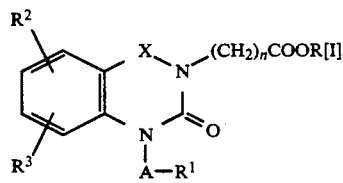

[Wherein R is hydrogen or a protecting group for carboxyl group, $R^1$ is a lower alkyl group, alkenyl group, alkynyl group, lower alkoxy group, lower alkylthio group, halogen, phenyl group (this phenyl group may be substituted by one to three of lower alkyls, lower alkoxys, halogens, trifluoromethyls, carboxyethylenes or ethoxycarbonylethylenes), naphthyl group, heterocycles (these heterocycles may be substituted by one to three of lower alkyls), cycloalkyl group or benzoyl group (this benzoyl group may be substituted by lower alkyl or halogen), $R^2$ and $R^3$ are identically or differently hydrogens, halogens, lower alkyl groups, lower alkoxy groups, aralkyl groups which may be substituted, nitro groups, imidazolyl groups, imidazolylmethyl groups or

($R^4$ and $R^5$ indicate identically or differently hydrogens or lower alkyl groups, or connected with each other to make five- or six-membered heterocycles which may contain other hetero atom, X is carbonyl, thiocarbonyl or methylene group (this methylene group may be substituted by lower alkyl group), A is lower alkylene or lower alkenylene, and n indicates an integer of 1 to 3],
or their salts have excellent inhibitory effect on platelet aggregation and strong inhibitory effect on aldose reductase, leading to the completion of the invention.

As "lower alkyl" shown in the invention, straight chain or branched one with carbon atoms of 1 to 6 such as methyl, ethyl, n-propyl or isopropyl can be mentioned. As "lower alkoxy", one with carbon atoms of 1 to 3 such as methoxy, ethoxy, n-propoxy or isopropoxy can be mentioned. As "lower alkylthio", one with carbon atoms of 1 to 3 such as methylthio, ethylthio or n-propylthio can be mentioned. As "halogen", fluorine, chlorine, bromine or iodine can be mentioned.

As "five-membered or six-membered heterocycle combined $R^4$ and $R^5$ one another, which may contain additional hetero atoms", for example, pyrrolidinyl, piperidino, morpholino, thiazolidyl, imidazolyl, etc. can be mentioned. "Cycloalkyl" means an alicyclic hydrocarbon with carbon atoms of 3 to 6 and, for example, cyclopropyl, cyclobutyl, cyclopentyl and cyclohexyl can be mentioned. "Heterocycle" means a saturated or unsaturated, monocyclic or polycyclic heterocyclic group capable of containing one or more oxygens, sulfurs and nitrogens and, for example, pyridyl, imidazolyl, thienyl, isoxazolyl, etc. can be mentioned. "Alkenyl" means a straight chain or branched group with carbon atoms of 2 to 6, which contains at least one unsaturated bond, for example, ethenyl, propenyl, isopropenyl, butenyl, etc. can be mentioned. "Alkynyl" means a straight chain or branched group with carbon atoms of 2 to 6, which contains at least one triple bond, for example, ethynyl, propargyl, butynyl, pentynyl, etc. can be mentioned. As the "protecting group for carboxyl group", lower alkyl, alkyl bearing phenyl group which may be substituted, alkoxyalkyl, hydroxyalkyl, tetrahydrofuranyl, tetrahydropyranyl, pivaloyloxymethyl, etc. can be mentioned. "Eliminating group" shown by Z is halogen (e.g. chlorine, bromine or iodine) or substituted sulfonyloxy (e.g. methanesulfonyloxy or benzenesulfonyloxy) or hydroxy and preferable one is halogen. "Lower alkylene" is one with carbon atoms of 1 to 6, such as methylene, ethylene, trimethylene, tetramethylene, etc. can be mentioned. "Lower alkenylene" differs from "lower alkylene" only in having unsaturated bond. "Their salts" in the invention mean salts permissible as medicinal drugs and salts with cations such as sodium, potassium, calcium, magnesium, etc. Moreover, some ones among the compounds of the invention show amphoteric property. In such cases, their salts can include salts with inorganic acids (hydrochloric acid, sulfuric acid, etc.) or with organic acids (p-toluenesulfonic acid, acetic acid, etc.).

According to the invention, compounds of the general formula [I] can be prepared through the processes shown below.

1-a) Compounds represented by the general formula [I] can be obtained by reacting compounds represented by a general formula [II]

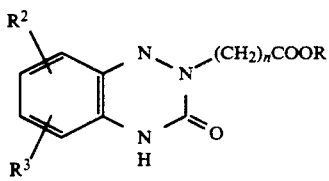

[wherein R, $R^2$, $R^3$, X and n are as described above], with compounds represented by a general formula [III]

 [III]

[wherein Z indicates an eliminating group and $R^1$, and A are as described above], in the presence of a suitable base. This reaction can be conducted advantageously in a solvent such as ethanol, dimethylformamide or dimethyl sulfoxide and in the presence of alkali metal hydride such as, for example, sodium hydride, lower alkoxide such as, for example, sodium ethoxide or the like, alkali metal hydroxide such as, for example, sodium hydroxide, alkali metal carbonate such as, for example, potassium carbonate or organic base such as, for example, pyridine, triethylamine or the like as a base. At this time, adding of catalytic amount to equimolar amount of alkali metal iodide such as sodium iodide is advantageous in order to promote the reaction. The reaction temperature is made to be within a range of 50° to 120° C. and the reaction completes in 2 to 10 hours.

Parts of the raw material compounds represented by the general formula [II] are publicly known, but they can be synthesized advantageously through the process below.

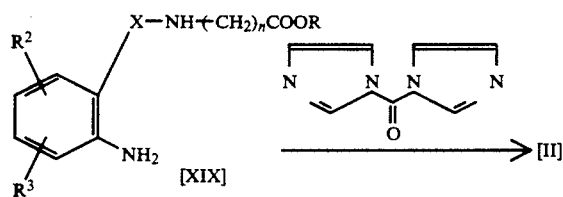

[wherein R, $R^2$, $R^3$, X and n are as described above].

Namely, they can be obtained by heating compounds represented by a general formula [XIX] with N, N'-carbonyldiimidazole at 80° to 160° C. in a solvent such as dimethylformamide or dioxane or without solvent.

1-b) Also, compounds of the general formula [I] can be obtained by reacting compounds represented by a general formula [IV]

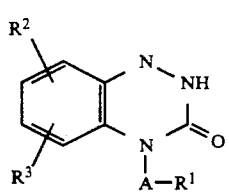

[wherein $R^1$, $R^2$, $R^3$, X, A and n are as described above], with compounds represented by a general formula [V]

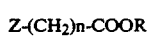 [V]

[wherein R, n and Z are as described above], in the presence of a suitable base.

This reaction can be conducted advantageously in a solvent such as ethanol, dimethylformamide or dimethyl sulfoxide and in the presence of said alkali metal hydride, lower alkoxide, alkali metal hydroxide, alkali metal carbonate or organic base as a base. In this case, sodium hydride or potassium carbonate is preferable. At this time, adding of alkali metal iodide is advantageous in order to promote the reaction.

The raw material compounds represented by the general formula [IV] are publicly known in part, but they can be synthesized through the process below.

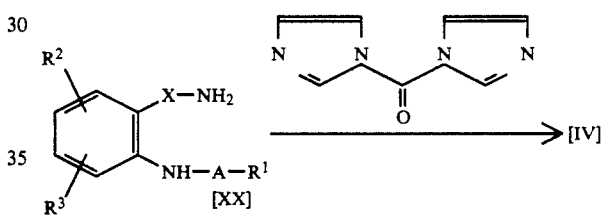

[wherein $R^1$, $R^2$, $R^3$, X and A are as described above].

Namely, they can be obtained by heating compounds represented by a general formula [XX] with N,N'-carbonyldiimidazole at 80° to 150° C. in a solvent such as dimethylformamide or dioxane or without solvent.

1-c) Compounds of the general formula [I] can be obtained by heating compounds represented by a general formula [VI]

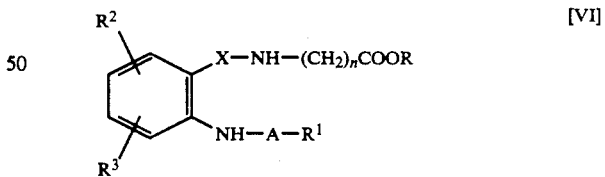

[wherein R, $R^1$, $R^2$, $R^3$, X, A and n are as described above], with N,N'-carbonyldiimidazole at 80° to 150° C. in a solvent such as dimethylformamide, dioxane or the like or without solvent. N,N'-carbonyldiimidazole is preferable to be used in amount of equimole or more. The reaction completes in 1 to 5 hours.

2) Compounds, R being hydrogen in the general formula [I], can be obtained by hydrolyzing the ester type protecting group for carboxylic acid. This hydrolysis can be conducted in the presence of base or acid. Preferable bases are alkali metal hydroxides (e.g. sodium hydroxide, potassium hydroxide, etc.) and the hydrolysis is carried out within a temperature range from room temperature to boiling point of solvent. As the acids, organic acids such as, for example, formic acid, acetic acid, propionic acid, benzenesulfonic acid, etc., inorganic acids such as, for example, hydrochloric acid, hydrobromic acid, sulfuric acid, etc., or their mixtures can be used. This reaction is usually performed under heating using an excess amount of acid.

In both cases, as the reaction solvent, water, acetone, methanol, ethanol, propanol or dimethylformamide is used.

3) Compounds represented by a general formula [VIII]

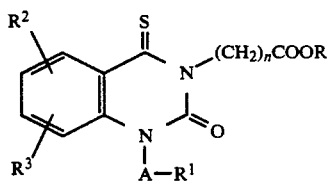

[wherein R, $R^1$, $R^2$, $R^3$, A and n are as described above], can be obtained by reacting compounds represented by a general formula [IX]

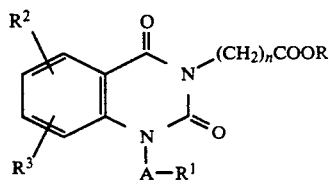

[wherein R, $R^1$, $R^2$, $R^3$, A and n are as described above], which are obtainable by the methods under 1-a) to c) and 2) aforementioned, with a suitable sulfide. As the sulfides to be used for this reaction, for example, Lawesson's reagent, phosphorus pentasulfide, etc. can be mentioned.

This reaction is conducted usually under nonaqueous concitions and in a common solvent being inert to the reaction such as chloroform, methylene chloride, dioxane, carbon disulfide, benzene, toluene or the like, using not less than equimol, preferably two to five times moles of said sulfide. The reaction temperature is within a range from room temperature to 120° C. and the reaction completes by continuing for 1 to 5 hours.

4) Moreover, compounds, R indicating a protecting group for carboxyl group in the general formula [I], can be obtained by reacting compounds represented by a general formula [X]

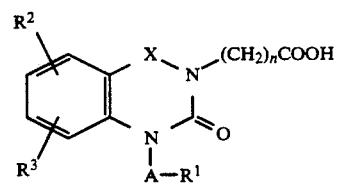

[wherein $R^1$, $R^2$, $R^3$, X, A and n are as described above], with compounds represented by a general formula [XI]

R'-Z [XI]

[wherein R' indicates a protecting group for carboxyl group and Z is as described above], in the presence of a suitable base. As the bases to be used for this reaction, alkali metals such as, for example, lithium, sodium, etc., alkali metal hydrides such as, for example, sodium hydride etc., alkali metal hydroxides such as, for example, sodium hydroxide, potassium hydroxide, etc., alkali metal carbonates such as, for example, sodium carbonate, potassium carbonate, etc., alkali metal alkoxides such as, for example, sodium methoxide etc. and organic bases such as, for example, triethylamine and pyridine can be mentioned. Usually, this reaction is conducted in a solvent being inert to the reaction such as acetone, dimethyl formamide, chloroform or the like within a range from room temperature to 120° C. and it completes in 30 minutes to 2 hours.

Compounds, R indicating a protecting group for carboxyl group in the general formula [I], can also be obtained by reacting reactive derivatives of compounds represented by the general formula [X] with compounds represented by a general formula [XII]

R'-OH [XII]

[wherein R' is as described above]. For example, they can be obtained by reacting reactive derivatives of [X], for example, acid halides etc. with lower alcohol such as methanol, ethanol or the like, aralkyl alcohol such as, for example, benzyl alcohol or the like, hydroxy lower alcohol such as, for example, ethylene glycol, methoxyethyl alcohol or the like, in which hydroxyl group may be substituted, or the like in an aprotic solvent such as, for example, chloroform, tetrahydrofuran, dimethylformamide or the like or without solvent.

5) Compounds represented by a general formula [XIII]

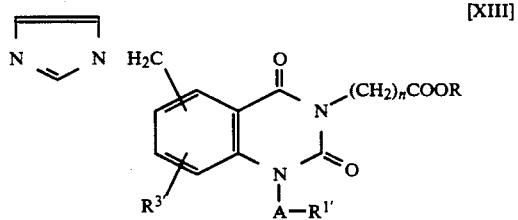

[wherein $R^{1'}$, is phenyl group (this phenyl group may be substituted by one to three of lower alkyls, lower alkoxys, halogens, trifluoromethyls, carboxyethylenes or ethoxycarbonylethylenes), $R^{3'}$ is hydrogen, halogen or lower alkoxy group and R, A and n are as described above], can be obtained by condensing imidazole with compounds represented by a general formula [XV]

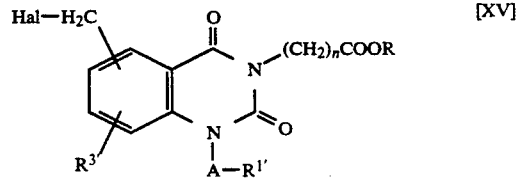

[wherein Hal is halogen and R, $R^{1'}$, $R^{3'}$, A and n are as described above], which are obtained by halogenation of compounds represented by general formula [XIV]

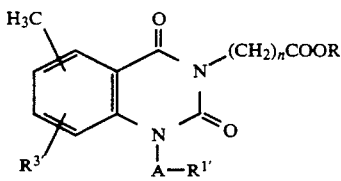

[wherein R, R$^{1'}$, R$^{3'}$, A and n are as described above], with halogenating agent such as chlorine, bromine, N-chlorosuccinimide or the like. The halogenation can be usually conducted advantageously in a solvent such as carbon tetrachloride, acetic acid, chloroform or the like, using peroxide such as benzoyl peroxide or the like or under the irradiation of light. The reaction is made within a temperature range from room temperature to boiling point of solvent and it completes in 2 to 6 hours. The condensation with imidazole can be achieved by heating at 80° to 120° C. in a solvent such as dioxane, dimethylformamide, dimethylacetamide or the like in the presence of a suitable base. As the bases, alkali metal carbonates such as potassium carbonate, sodium carbonate, etc. or imidazole itself are desirable.

6) Compounds represented by a general formula [XVI]

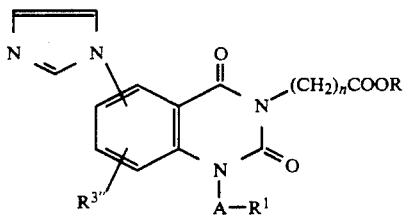

[wherein R$^{3''}$ is hydrogen, halogen, lower alkyl group, lower alkoxy group, aralkyl group which may be substituted or nitro group and R, R$^1$, A and n are as described above], can be obtained by reacting compounds represented by a general formula [XVIII]

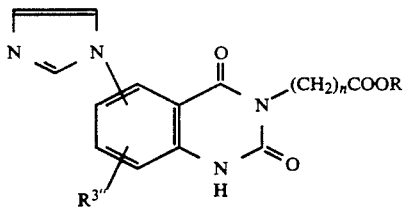

[wherein R, R$^{3''}$ and n are as described above], which are obtainable by heating compounds represented by a general formula [XVII]

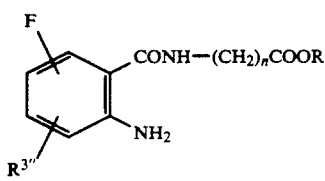

[wherein R, R$^{3''}$ and n are as described above], with equimole or more N,N$^1$-carbonyldiimidazole at 100° to 160° C. in dioxane or dimethylformamide or without solvent, with compounds represented by a general formula [III]

$$R^1\text{-A-Z} \qquad [III]$$

[wherein R$^1$, A and Z are as described above], under similar conditions to 1-a).

Compounds represented by the general formula [XVII] can be obtained by condensing 4,5-difluoroisatoic anhydride with aminoalkanic acid or its ester (e.g. glycine, 2-aminopropionic acid, alanine, etc. their ester derivatives and their salts).

This reaction is conducted within a temperature range from room temperature to 70° C. in ethanol, dioxane or mixtures of these solvents with water in the presence of a suitable base (e.g. potassium carbonate, sodium carbonate, triethylamine, piperidine, pyridine, etc.).

The compounds obtainable through the processes as above can be isolated and purified by publicly known separating and purifying means, for example, by solvent extraction, recrystallization, chromatography, etc.

When salts of compounds represented by the general formula [I], which are pharmaceutically permissible, are further required, they can be obtained by reacting with base coexisting cation such as, for example, sodium hydroxide, potassium hydroxide or the like, inorganic acid such as, for example, hydrochloric acid, sulfuric acid or the like, or organic acid such as, for example, fumaric acid, oxalic acid or the like according to usual method. Best embodiment for putting the invention into practice.

The preparation examples and the examples of the invention will be described to illustrate the invention in more detail.

REFERENTIAL EXAMPLE 1

Ethyl (2-amino-5-chlorobenzoyl)aminoacetate

Into a mixed liquor of 160 ml of dioxane with 40 ml of water were dissolved 10.5 g of glycine ethyl ester hydrochloride, and 11.9 g of 6-chloro-2H-3,1-benzoxazine-2,4(1H)-dione were added. To this were added dropwise 8.1 g of triethylamine at room temperature under stirring, and the mixture was stirred for 30 minutes. After stirring further for 1 hour, dioxane was distilled off and 100 ml of water were added. The deposits were collected by filtration, washed with water and dried. Then, these were recrystallized from carbon tetrachloride to obtain 11.0 g of title compound, m.p. 108°–110° C.

Elemental analysis (%) as $C_{11}H_{13}ClN_2O_3$: Calculated: C: 51.47 H: 5.10 N: 10.92. Observed: C: 51.27 H: 5.08 N: 10.88.

REFERENTIAL EXAMPLE 2

Ethyl 6-chloro-1,4-dihydro-2,4-dioxo-3(2H)-quinazolineacetate

Into 35 ml of dioxane were dissolved 27.6 g of compound of Referential example 1, and, after added 35 g of N,N'-carbonyldiimidazole, the mixture was heated to 150° C. After distilled off dioxane, the reaction mixture was heated further for 20 minutes under stirring. After cooling, methanol was added and the crystals deposited were collected by filtration and dried. They were recrystallized from dioxane to obtain 28.6 g of title compound. m.p. 214.0°–215.0° C.

Elemental analysis (%) as $C_{12}H_{11}ClN_2O_4$: Calculated: C: 50.98 H: 3.92 N: 9.91. Observed: C: 50.68 H: 3.84 N: 9.88.

REFERENTIAL EXAMPLE 3

2-(4-Chlorophenylmethylamino)benzamide

In 400 ml of concentrated aqueous ammonia, 14.4 g of 1-(4-chlorophenylmethyl)-2H-3,1-benzoxazine-2,4(1H)-dione were heated to 100° C. and stirred for 3 hours. After cooling, the crystals were collected by filtration, washed with water and dried. They were recrystallized from ethanol to obtain 8.6 g of title compound. m.p. 138°–139° C.

REFERENTIAL EXAMPLE 4

1-(4-Chlorophenylmethyl)quinazoline-2,4-(1H,3H)-dione

In 10 ml of dioxane, 3.5 g of compound of Referential example 3 and 4.4 g of N,N'-carbonyldiimidazol were heated to 150° C. After distilled off dioxane, the reaction mixture was heated further for 30 minutes under stirring. After cooling, it was permeated with methanol and the crystals deposited were collected by filtration and dried. They were recrystallized from dioxane to obtain 30 g of title compound. m.p. 217°–218° C.

Elemental analysis (%) as $C_{15}H_{11}ClN_2O_2$: Calculated: C: 62.83 H: 3.87 N: 9.77. Observed: C: 62.88 H: 3.70 N: 9.75.

REFERENTIAL EXAMPLE 5

Ethyl [2-[N-(2,4-dichlorophenyl)methyl]amino-5-methoxybenzoyl]aminoacetate

Into a mixed liquor of 150 ml of dioxane with 30 ml of water were dissolved 5.0 g of 1-(2,4-dichlorophenyl)-methyl-6-methoxy-2H-3,1-benzoxazine-2,4(1H)-dione, and 2.4 g of glycine ethyl ester hydrochloride were added and further 1.9 g of triethylamine were added dropwise. The mixture was refluxed for 3 hours. After cooling, solvent was distilled off, water was added, and the reaction mixture was extracted with ethyl acetate. It was dried and the solvent was distilled off to obtain 4.7 g of title compound as an oily product.

REFERENTIAL EXAMPLE 6

Ethyl (2-amino-4,5-difluorobenzoyl)aminoacetate

Into a mixed liquor of 280 ml of dioxane with 70 ml of water were dissolved 19 g of glycine ethyl ester hydrochloride, and 21.7 g of 6,7-difluoro-2H-3,1-benzoxazine-2,4(1H)-dione were added and 14.7 g of triethylamine were added dropwise at room temperature under stirring. After stirring further for 30 minutes, the mixture was heated to 70° C. and stirred for 1,5 hours. Dioxane was distilled off, 150 ml of water were added, then the crystals deposited were collected by filtration, washed with water, and dried. They were recrystallized from ethyl acetate to obtain 20 g of title compound. m.p. 147° C.

Elemental analysis (%) as $C_{11}H_{12}F_2N_2O_3$: Calculated: C: 51.16 H: 4.69 N: 10.58. Observed; C: 50.78 H: 4.31 N: 10.36.

EXAMPLE 1

Ethyl 6-chloro-1-(4-chlorophenyl)methyl-1,4-dihydro-2,4-dioxo-3(2H)-quinazolineacetate Into 30 ml of dimethylformamide were suspended 0.34 g of sodium hydride (60%), and 2.00 g of 6-chloro-1,4-dihydro-2,4-dioxo-3(2H)-quinazolineacetate were added. After stirring for 10 minutes at room temperature, 1.25 g of 2-chlorobenzyl chloride were added and the mixture was stirred for 20 minutes at room temperature and further for 1 hour at 70° C. After cooling, the reaction mixture was poured into water and the deposits were collected by filtration. They were recrystallized from ethanol to obtain 0.78 g of title compound. m.p. 137°–138° C.

Elemental analysis (%) as $C_{19}H_{16}Cl_2N_2O_4$: Calculated: C: 56.03 H: 3.96 N: 6.88. Observed; C: 56.12 H: 3.88 N: 6.77.

EXAMPLE 2

Ethyl 1-(4-bromo-2-fluorophenyl)methyl-6-chloro-1,4-dihydro-2,4-dioxo-3(2H)-quinazolineacetate Into 250 ml of dried dimethylformamide were dissolved 10 g of ethyl 6-chloro-1,4-dihydro-2,4-dioxo-3(2H)-quinazolineacetate, and 4.86 g of potassium carbonate were added and 10.40 g of 4-bromo-2-fluorobenzyl bromide were added under stirring. After stirring for 1 hour at 60° C., the reaction mixture was poured into 400 ml of ice water and the crystals were collected by filtration. They were recrystallized from ethanol to obtain 12.0 g of title compound. m.p. 145°–146° C.

Elemental analysis (%) as $C_{19}H_{15}BrFN_2O_4$: Calculated: C: 48.59 H: 3.22 N: 5.96. Observed: C: 48.54 H: 3.18 N: 5.96.

Example 3–79

Following compounds were obtained through similar processes to Example 1 and 2.

| Example | $R^n$ | A | $R^1$ | m.p. (°C.) (Recryst. solvent) |
|---|---|---|---|---|
| 3 | 6-Cl | —CH$_2$— | 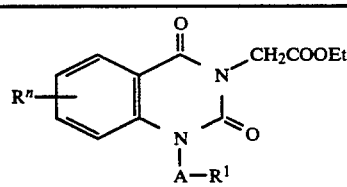 | 146–148 (EtOH) |

-continued
| | | | | |
|---|---|---|---|---|
| 4 | 6-Cl | —CH₂— | 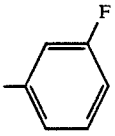 | 130–132 (EtOH) |
| 5 | 6-Cl | —CH₂— | 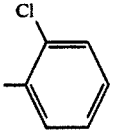 | 137–138 (EtOH) |
| 6 | 6-Cl | —CH₂— | 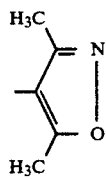 | 166–168 (EtOH) |
| 7 | 6-Cl | —CH₂— | 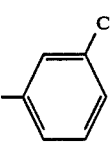 | 161–162 (CH₃CN) |
| 8 | 6-Cl | —CH₂— | 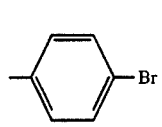 | 138–139 (EtOH) |
| 9 | 6-Cl | —CH₂— | 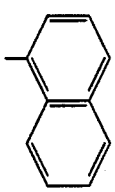 | 176–178 (CH₃CN) |
| 10 | 6-Cl | —CH₂— | 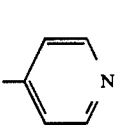 | 174–175 (EtOH) |
| 11 | 6-Cl | —CH₂— | 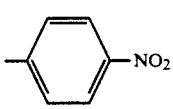 | 177–178 (CH₃CN) |
| 12 | 6-Cl | —CH₂— | 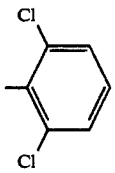 | 174–175 (CH₃CN) |
| 13 | H | —CH₂— | 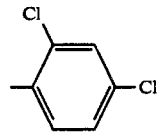 | 114–115 (EtOH) |
| 14 | 6-F | —CH₂— | 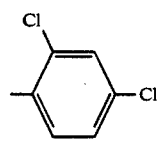 | 134.5–135.5 (CH₃CN) |

-continued

| | | | | |
|---|---|---|---|---|
| 15 | 6-F | —CH$_2$— | 3,4-diClC$_6$H$_3$ | 160–161 (CH$_3$CN) |
| 16 | 6-Cl | —CH$_2$— | 3,4-diClC$_6$H$_3$ | 153–154 (EtOH) |
| 17 | 6-Cl | —CH$_2$— | C$_6$H$_5$ | 144–145 (CH$_3$CN) |
| 18 | 6-Cl | —CH$_2$— | cyclohexyl | 134–136 (EtOH) |
| 19 | H | —CH$_2$— | 3,4-diClC$_6$H$_3$ | 142–143 (EtOH) |
| 20 | 6-Cl | —CH$_2$— | 2,4-diFC$_6$H$_3$ | 149 (CH$_3$CN) |
| 21 | 6-F | —CH$_2$— | 2,4-diFC$_6$H$_3$ | 127–128 (EtOH) |
| 22 | 7-Cl | —CH$_2$— | 2,4-diClC$_6$H$_3$ | 167–168 (CH$_3$CN) |
| 23 | 6,7-(OCH$_3$)$_2$ | —CH$_2$— | 2,4-diClC$_6$H$_3$ | 176–178 (CH$_3$CN) |
| 24 | 6-Cl | —CH$_2$— | 4-CH$_3$C$_6$H$_4$ | 142–143 (Cyclohexane) |
| 25 | 6-Cl | —CH$_2$— | 4-CF$_3$C$_6$H$_4$ | 165–166 (EtOH) |
| 26 | 6-Cl | —CH$_2$— | 3,4-diFC$_6$H$_3$ | 165–166.5 (CH$_3$CN) |

| | | | | |
|---|---|---|---|---|
| 27 | 7-Cl | —CH$_2$— | 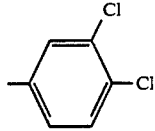 | 180–181 (CH$_3$CN) |
| 28 | 6-Cl | —CH$_2$— | 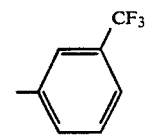 | 147–148 (EtOH) |
| 29 | H | —CH$_2$— | 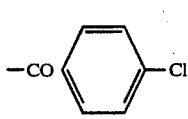 | 196 (CH$_3$CN) |
| 30 | H | —CH$_2$CH=CH— | 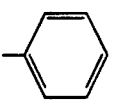 | 96–97 (EtOH) |
| 31 | 6-CH$_3$ | —CH$_2$— | 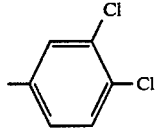 | 167 (EtOH) |
| 32 | H | —CH$_2$— | 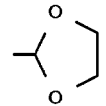 | 161–162 (CH$_3$CN) |
| 33 | 6,7-(OCH$_3$)$_2$ | —CH$_2$— | 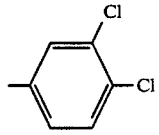 | 128–129 (CH$_3$CN) |
| 34 | 6-Br | —CH$_2$— | 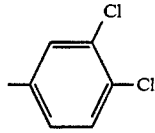 | 168 (CH$_3$CN) |
| 35 | 6-Br | —CH$_2$— | 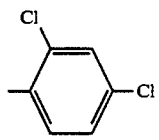 | 164–164.5 (CH$_3$CN) |
| 36 | 6-CH$_3$ | —CH$_2$— | 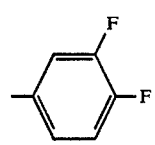 | 168 (EtOH) |
| 37 | H | —CH$_2$— | 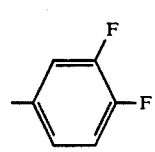 | 138–139 (EtOH) |
| 38 | 6-Cl | —CH$_2$CH=CH— | 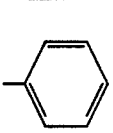 | 107–108 (EtOH) |

| | | | | |
|---|---|---|---|---|
| 39 | 6-Cl | —CH₂— | 2,4-dimethylphenyl (CH₃, CH₃) | 120–121 (EtOH) |
| 40 | 6-Cl | —CH₂— | 3,4-dimethoxyphenyl (OCH₃, OCH₃) | 154–155 (EtOH) |
| 41 | 6-F | —CH₂— | 3,4-difluorophenyl (F, F) | 147 (EtOH) |
| 42 | 5-Cl | —CH₂— | 3,4-dichlorophenyl (Cl, Cl) | 161–162 (EtOH) |
| 43 | 5-Cl | —CH₂— | 3,4-difluorophenyl (F, F) | 163–164 (EtOH) |
| 44 | 6,8-Cl₂ | —CH₂— | 3,4-dichlorophenyl (Cl, Cl) | 107–109 (EtOH) |
| 45 | 6-Cl | —CH₂— | 3,4,5-trimethoxyphenyl (OCH₃, OCH₃, OCH₃) | 141–142 (EtOH) |
| 46 | 6-Cl | —CH₂CH₂— | —OCH₂CH₃ | 94–95 (Benzene-hexane) |
| 47 | 6,7-(OCH₃)₂ | —CH₂— | 3,4-dimethoxyphenyl (OCH₃, OCH₃) | 152–153 (CH₃CN) |
| 48 | 6-Cl | —CH₂— | —CH(CH₃)₂ | 104–105 (EtOH) |
| 49 | 6-Et | —CH₂— | 3,4-dichlorophenyl (Cl, Cl) | 140–141 (EtOH) |
| 50 | 6-NO₂ | —CH₂— | 3,4-dichlorophenyl (Cl, Cl) | 155–156 (EtOH) |
| 51 | 6-Cl | —CH₂— | —CCH | 118–119 (EtOH) |

-continued

| | | | | |
|---|---|---|---|---|
| 52 | 6-Cl | —CH$_2$— | 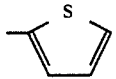 (thiophen-2-yl) | 131 (EtOH) |
| 53 | 6-Et | —CH$_2$— | 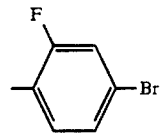 (4-bromo-2-fluorophenyl) | 125–126 (EtOH) |
| 54 | 6,7-(OCH$_3$)$_2$ | —CH$_2$— | 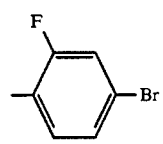 (4-bromo-2-fluorophenyl) | 153–155 (EtOH) |
| 55 | 6-F | —CH$_2$— | 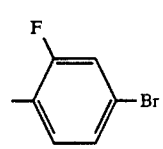 (4-bromo-2-fluorophenyl) | 161 (CH$_3$CN) |
| 56 | 6-CH$_3$ | —CH$_2$— | 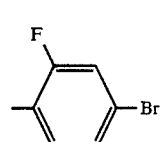 (4-bromo-2-fluorophenyl) | 156–158 (CH$_3$CN) |
| 57 | 5-Cl | —CH$_2$— | 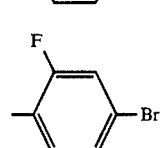 (4-bromo-2-fluorophenyl) | 156 (EtOH) |
| 58 | 7-Cl | —CH$_2$— | 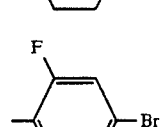 (4-bromo-2-fluorophenyl) | 155–156 (EtOH) |
| 59 | 6-Br | —CH$_2$— | 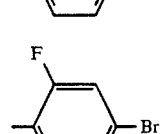 (4-bromo-2-fluorophenyl) | 147–148 (EtOH) |
| 60 | 6-Cl | —CH$_2$CH$_2$CH$_2$— | 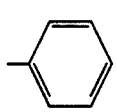 (phenyl) | 88–89 (Cyclohexane) |
| 61 | 6-Cl | —CH$_2$CH$_2$CH$_2$— | 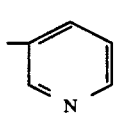 (pyridin-3-yl) | 104–105 (EtOH) |
| 62 | 6-OCH$_2$- 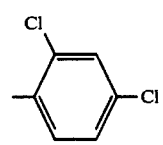 (2,4-dichlorophenyl) | —CH$_2$— | 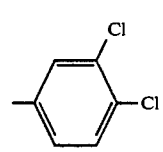 (2,4-dichlorophenyl) | 155–156 (EtOH) |
| 63 | 6-N(CH$_3$)$_2$ | —CH$_2$— | (3,4-dichlorophenyl) | 143–144 (EtOH) |

-continued
| Example | $R^n$ | A | $R^1$ | m.p. (°C.) (Recryst. solvent) |
|---|---|---|---|---|
| 64 | 6-Cl | —(CH$_2$)$_6$— | —Br | 67–68 (Et$_2$O) |
| 65 | 6-NO$_2$ | —CH$_2$— | 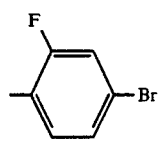 | 138–138.5 (EtOH) |
| 66 | 6-N | —CH$_2$— | 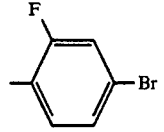 | 173–174 (CH$_3$CN) |
| 67 | 6-N(CH$_3$)$_2$ | —CH$_2$— | 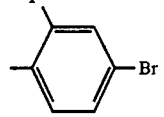 | 146–147 (EtOH) |
| 68 | 6-OCH$_3$ | —CH$_2$— | 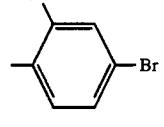 | 129–130 (EtOH) |
| 69 | 6-N | —CH$_2$— | 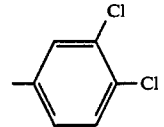 | 144–145 (EtOH) |
| 70 | 6-SCH$_3$ | —CH$_2$— | 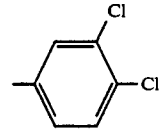 | 114–115 (EtOH) |
| 71 | 6-Cl | —(CH$_2$)$_6$— | —(CH$_2$)$_3$CH$_3$ | 35–40 (n-Hexane) |
| 72 | 6-Cl | —(CH$_2$)$_6$— | —CH$_2$CH$_3$ | Oily product |
| 73 | 6-Cl | —(CH$_2$)$_4$— | —CH$_3$ | 75–77 (EtOH) |
| 74 | 6-OCH$_3$ | —CH$_2$— | 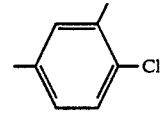 | 130–131 (EtOH) |
| 75 | 5-Cl | —CH$_2$— | 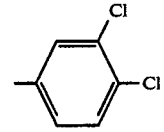 | 155–156 (EtOH) |
| 76 | 6-Cl | —CH$_2$— | 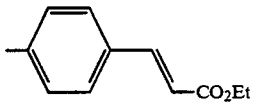 | 155–157 (EtOH) |
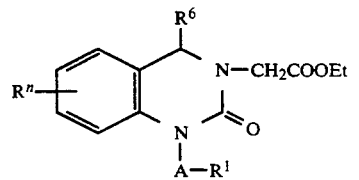
| Example | $R^n$ | $R^6$ | A | $R^1$ | m.p. (°C.) (Recryst. solvent) |
|---|---|---|---|---|---|

| | | | | | |
|---|---|---|---|---|---|
| 77 | H | —CH₃ | —CH₂— | 2,3-diClC₆H₃ | Oily product |
| 78 | H | H | —CH₂— | 2,3-diClC₆H₃ | 97–98 (EtOH) |
| 79 | 6-CH₃ | H | —CH₂— | 2,3-diClC₆H₃ | 121–122 (EtOH) |

Example 80

Ethyl 1-(4-chlorophenyl)methyl-1,4-dihydro-2,4-dioxo-3(2H)-quinazolineacetate

Into 20 ml of dried dimethylformamide were suspended 0.24 g of sodium hydride, and after added 1.43 g of 1-(4-chlorophenyl)-methyl-3H-quinazoline-2,4-dione to this, the mixture was stirred for 15 minutes. Thereafter, 0.92 g of ethyl bromoacetate were further added dropwise and the mixture was stirred for 2 hours at room temperature. After cooling by allowed to stand, the reaction mixture was poured into 500 ml of water and the deposits were collected by filtration. They were recrystallized from ethanol to obtain 1.29 g of title compound. m.p. 138°–139° C.

Elemental analysis (%) as $C_{19}H_{17}ClN_2O_4$: Calculated: C: 61.21 H: 4.60 N: 7.52. Observed: C: 61.12 H: 4.45 N: 7.48.

EXAMPLE 81–84

Following compounds were obtained through similar process to Example 80.

| Example | $R^n$ | A | $R^1$ | n | m.p. (°C.) (Recryst. solvent) |
|---|---|---|---|---|---|
| 81 | H | —CH₂— | 4-ClC₆H₄ | 2 | 98–100 (EtOH) |
| 82 | 6-Cl | —CH₂— | 3,4-diClC₆H₃ | 1 | 168–168.5 (EtOH) |
| 83 | H | —CH₂— | 3,4-diClC₆H₃ | 2 | 117–118 (EtOH) |
| 84 | H | —CH₂— | 2,4-diClC₆H₃ | 3 | 109–110 (EtOH) |

EXAMPLE 85

1-(4-Bromo-2-fluorophenyl)methyl-6-chloro-1,4-dihydro-2,4-dioxo-3(2H)-quinazolineacetic acid.

Into 280 ml of concentrated hydrochloric acid and 140 ml of acetic acid were suspended 18.0 g of ethyl 1-(4-bromo-2-fluorophenyl)methyl-6-chloro-1,4-dihydro-2,4-dioxo-3(2H)quinazolineacetate, and, after added 1 ml of concentrated sulfuric acid, the mixture was refluxed for 3 hours. After cooling, the reaction liquor was poured into 600 ml of ice water and the deposits were collected by filtration. They were recrystallized from ethanol to obtain 15.0 g of title compound. m.p. 189° C.

Elemental analysis (%) as $C_{17}H_{11}BrClFN_2O_4$: Calculated: C: 46.23 H: 2.51 N: 6.34 Observed: C: 46.28 H: 2.38 N6.30

Example 86

6-Chloro-1-(4-fluorophenyl)methyl-1,4-dihydro2,4-dioxo-3(2H)-quinazolineacetic acid Into 50 ml of ethanol were dissolved 1.59 g of ethyl 6-chloro-1-(4-fluorophenyl)methyl-1,4dihydro-2,4-dioxo-3(2H)-quinazolineacetate, and after added 5 ml of aqueous solution containing 0.30 g of potassium hydroxide, the mixture was refluxed for 1 hour. After cooling by allowing to stand, ethanol was distilled off and the residue was dissolved by adding 30 ml of water, acidified with concentrated hydrochloric acid, and the deposits were collected by filtration. They were recrystallized from acetonitrile to obtain 0.75 g of title compound. m.p. 211°–212° C.

Elemental analysis (%) as $C_{17}H_{12}ClFN_2O_4$: Calculated: C: 56.28 H: 3.34 N: 7.72. Observed: C: 56.26 H: 3.29 N: 7.68.

EXAMPLE 87–175

Following compounds were obtained through similar processes to Example 85 and 86.

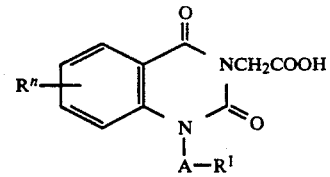

| Example | $R^n$ | A | $R^1$ | m.p. (°C.) (Recryst. solvent) |
|---------|-------|-----|-------|-------------------------------|
| 87 | H | —CH$_2$— | 4-Cl-phenyl | 222–223 (EtOH) |
| 88 | 6-Cl | —CH$_2$— | 2,4-diCl-phenyl | 204–205 (CH$_3$CN) |
| 89 | 6-Cl | —CH$_2$— | 3,4-diCl-phenyl | 118–120 (CH$_3$CN) |
| 90 | 6-Cl | —CH$_2$— | 2-pyridyl | >300 (DMF) |
| 91 | 6-Cl | —CH$_2$— | 3-F-phenyl | 95–97 (EtOH) |
| 92 | 6-Cl | —CH$_2$— | 2-Cl-phenyl | 257–258 (EtOH) |
| 93 | 6-Cl | —CH$_2$— | 3,5-diMe-isoxazolyl | 256–257 (AcOH) |
| 94 | 6-Cl | —CH$_2$— | 3-Cl-phenyl | 117–119 (CH$_3$CN) |
| 95 | 6-Cl | —CH$_2$— | 4-Br-phenyl | 225–226 (AcOH) |

| | | | | |
|---|---|---|---|---|
| 96 | 6-Cl | —CH$_2$— | 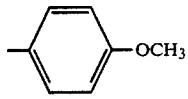 | 208–209 (AcOH) |
| 97 | 6-OCH$_3$ | —CH$_2$— | 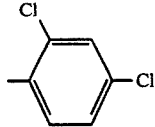 | 238–239 (EtOH) |
| 98 | 6-Cl | —CH$_2$— | 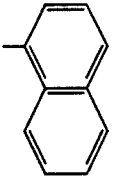 | 239–240 (AcOH) |
| 99 | 6-Cl | —CH$_2$— | 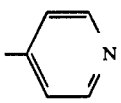 | 174 (EtOH) |
| 100 | 6-Cl | —CH$_2$— | 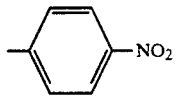 | 245–246 (EtOH) |
| 101 | 6-Cl | —CH$_2$— | 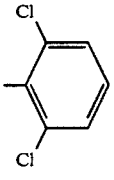 | 291–292 (AcOH) |
| 102 | 6-CH$_3$ | —CH$_2$— | 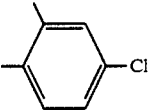 | 232–233 (iPrOH) |
| 103 | H | —CH$_2$— | 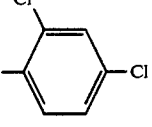 | 201–202 (AcOH) |
| 104 | 6-F | —CH$_2$— | 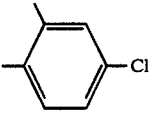 | 184–185 (CH$_3$CN) |
| 105 | 6-F | —CH$_2$— | 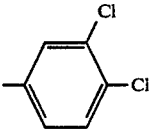 | 206–207 (CH$_3$CN) |
| 106 | 6-Cl | —CH$_2$— | 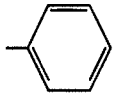 | 222–223 (CH$_3$CN) |

| | | | | |
|---|---|---|---|---|
| 107 | 6-Cl | —CH₂CH₂— |  | 223–225 (CH₃CN) |
| 108 | 6-Cl | —CH₂— | 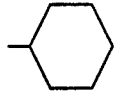 | 198–199 (Benzene) |
| 109 | H | —CH₂— | 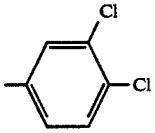 | 182–185 (Benzene) |
| 110 | 6-Cl | —CH₂— | 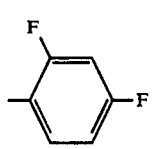 | 233–234 (EtOH) |
| 111 | 6-F | —CH₂— | 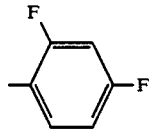 | 190–191 (EtOH) |
| 112 | 7-Cl | —CH₂— | 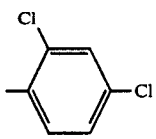 | 238–239 (EtOH) |
| 113 | 6,7-(OCH₃)₂ | —CH₂— | 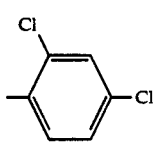 | 247–248 (AcOH) |
| 114 | 6-Cl | —CH₂— | 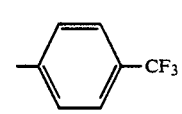 | 204–205 (CH₃CN) |
| 115 | 6-Cl | —CH₂— | 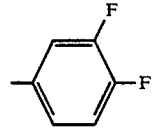 | 216–217 (CH₃CN) |
| 116 | 7-Cl | —CH₂— | 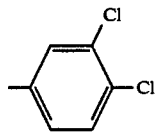 | 199–200 (CH₃CN) |
| 117 | 6-Cl | —CH₂— | 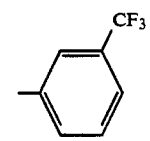 | 173–174 (Benzene) |
| 118 | 6-Cl | —CH₂— | 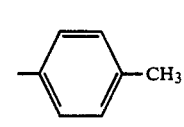 | 195–200 (Benzene) |

-continued
| | | | | |
|---|---|---|---|---|
| 119 | H | —CH$_2$— | 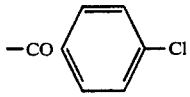 | 212–213 (EtOH) |
| 120 | H | —CH$_2$CH=CH— | 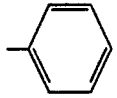 | 175–176 (Benzene) |
| 121 | 6-CH$_3$ | —CH$_2$— | 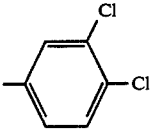 | 217–219 (EtOH) |
| 122 | H | —CH$_2$— | 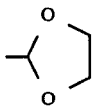 | 251–252 (Dioxane) |
| 123 | 6,7-(OCH$_3$)$_2$ | —CH$_2$— | 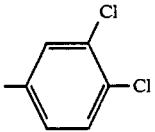 | 197–198 (EtOH) |
| 124 | H | —CH$_2$— | 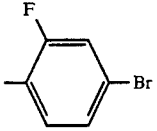 | 172–173 (EtOH) |
| 125 | 6-Br | —CH$_2$— | 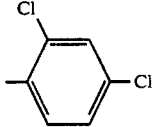 | 219–220 (Toluene) |
| 126 | 6-Br | —CH$_2$— | 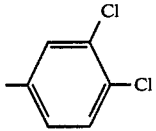 | 193–194 (Benzene) |
| 127 | 6-CH$_3$ | —CH$_2$— | 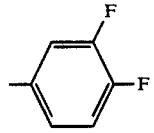 | 178 (CH$_3$CN) |
| 128 | H | —CH$_2$— | 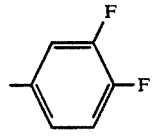 | 171–172 (CH$_3$CN) |
| 129 | 6-Cl | —CH$_2$CH=CH— | 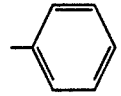 | 169–171 (Benzene) |
| 130 | 6-Cl | —CH$_2$— | 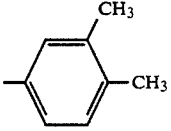 | 194–195 (Toluene) |

-continued

| | | | | |
|---|---|---|---|---|
| 131 | 6-F | —CH₂— | 3,4-difluorophenyl | 168–170 (Toluene) |
| 132 | 5-Cl | —CH₂— | 3,4-dichlorophenyl | 135–137 (CH₃CN) |
| 133 | 5-Cl | —CH₂— | 3,4-difluorophenyl | 200–201 (CH₃CN) |
| 134 | 6-Cl | —CH₂— | 3,4-dimethoxyphenyl | 202–205 (CH₃CN) |
| 135 | 6-NO₂ | —CH₂— | 3-fluoro-4-bromophenyl | 215–217 (EtOH) |
| 136 | 6-Cl | —CH₂— | 3,4,5-trimethoxyphenyl | 268–269 (CH₃CN) |
| 137 | 6-Cl | —CH₂CH₂— | —OCH₂CH₃ | 171–172 (Benzene) |
| 138 | 6,7-(OCH₃)₂ | —CH₂— | 3,4-dimethoxyphenyl | 225–226 (CH₃CN) |
| 139 | 6-Cl | —CH₂— | —CH(CH₃)₂ | 201–202 (Benzene-hexane) |
| 140 | 6-Et | —CH₂— | 3,4-dichlorophenyl | 226–227 (Toluene) |
| 141 | 6-Cl | —CH₂— | —CCH | 239–240 (EtOH) |
| 142 | 6-Cl | —CH₂— | 2-thienyl | 223 (EtOH) |
| 143 | 6-Et | —CH₂— | 3-fluoro-4-bromophenyl | 215–216 (Benzene) |

-continued
| | | | | |
|---|---|---|---|---|
| 144 | 6,7-(OCH$_3$)$_2$ | —CH$_2$— | 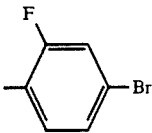 | 233–235 (CH$_3$CN) |
| 145 | 6-F | —CH$_2$— | 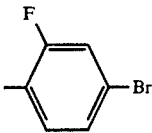 | 181–182 (EtOH) |
| 146 | 6-CH$_3$ | —CH$_2$— | 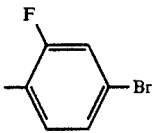 | 214–215 (EtOH) |
| 147 | 7-Cl | —CH$_2$— | 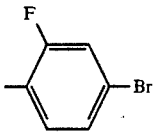 | 202–203 (AcOEt) |
| 148 | 5-Cl | —CH$_2$— | 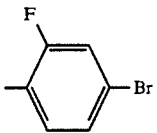 | 191–192 (CH$_3$CN) |
| 149 | 6-Br | —CH$_2$— | 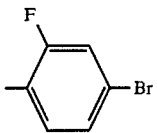 | 204–204.5 (CH$_3$CN) |
| 150 | 6-Cl | —CH$_2$CH$_2$— | 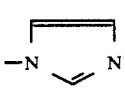 | >300 (DMF) |
| 151 | 6-Cl | —CH$_2$CH$_2$CH$_2$— | 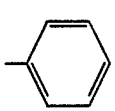 | 186–187 (EtOH) |
| 152 | 6-Cl | —CH$_2$CH$_2$CH$_2$— | 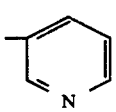 | 188–189 (Dioxane) |
| 153 | 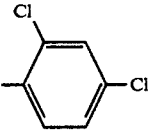 | —CH$_2$— | 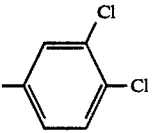 | 214–215 (AcOH) |
| 154 | 6-N(CH$_3$)$_2$ | —CH$_2$— |  | 197–198 (i-PrOH) |
| 155 | 6-Cl | —(CH$_2$)$_5$— | —CH$_3$ | 155–157 (Et$_2$O) |

-continued

| | | | | |
|---|---|---|---|---|
| 156 | 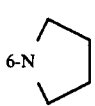6-N⟨pyrrolidine⟩ | —CH₂— | 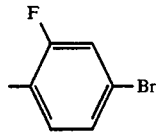 2-F, 4-Br phenyl | 248–249 (EtOH) |
| 157 | 6-N(CH₃)₂ | —CH₂— | 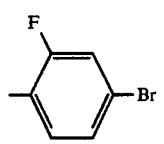 2-F, 4-Br phenyl | 211–212 (EtOH) |
| 158 | 6-N(CH₃)₂ | —CH₂— | 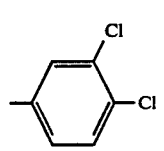 3,4-Cl₂ phenyl | 204–205 (CH₃CN) |
| 159 | 6-Cl | —CH₂— | 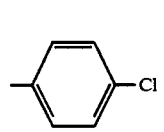 4-Cl phenyl | 226–228 (CH₃CN) |
| 160 | 6-OCH₃ | —CH₂— | 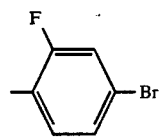 2-F, 4-Br phenyl | 218–219 (EtOH) |
| 161 | 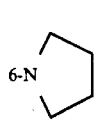6-N⟨pyrrolidine⟩ | —CH₂— | 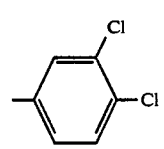 3,4-Cl₂ phenyl | 189–190 (EtOH) |
| 162 | 6-SCH₃ | —CH₂— | 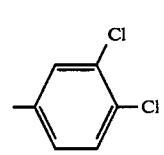 3,4-Cl₂ phenyl | 208–210 (EtOH) |
| 163 | 6-Cl | —(CH₂)₆— | —(CH₂)₃CH₃ | 79–81 (Cyclohexane) |
| 164 | 6-Cl | —(CH₂)₆— | —CH₂CH₃ | 118–121 (Et₂O) |
| 165 | 6-Cl | —(CH₂)₄— | —CH₃ | 129–131 (Toluene) |
| 166 | 6-OCH₃ | —CH₂— | 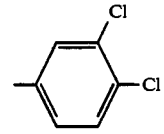 3,4-Cl₂ phenyl | 253–255 (EtOH) |
| 167 | 6,8-Cl₂ | —CH₂— | 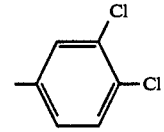 3,4-Cl₂ phenyl | 149–150 (Chloroform-hexane) |
| 168 | 5-Cl | —CH₂— | 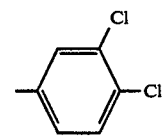 3,4-Cl₂ phenyl | 127–128 (Benzene) |
| 169 | 6-Cl | —CH₂— | 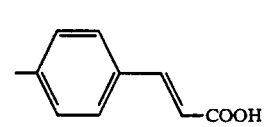 4-(CH=CH-COOH) phenyl | >300 (Dioxane-hexane) |

-continued

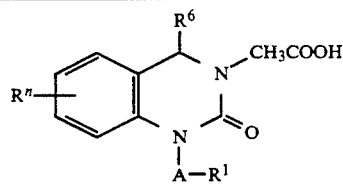

| Example | $R^n$ | $R^6$ | A | $R^1$ | m.p. (°C.) (Recryst. solvent) |
|---|---|---|---|---|---|
| 170 | H | —CH$_3$ | —CH$_2$— | 3,4-diCl-C$_6$H$_3$ | 157–158.5 (Et$_2$O-hexane) |
| 171 | H | H | —CH$_2$— | 3,4-diCl-C$_6$H$_3$ | 127–128 (AcOEt) |
| 172 | 6-CH$_3$ | H | —CH$_2$— | 3,4-diCl-C$_6$H$_3$ | 181–182 (CH$_3$CN) |

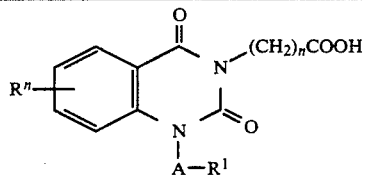

| Example | $R^n$ | A | $R^1$ | n | m.p. (°C.) (Recryst. solvent) |
|---|---|---|---|---|---|
| 173 | H | —CH$_2$— | 4-Cl-C$_6$H$_4$ | 2 | 197.5–198 (EtOH) |
| 174 | H | —CH$_2$— | 2,4-diCl-C$_6$H$_3$ | 2 | 192–193 (EtOH) |
| 175 | H | —CH$_2$— | 2,4-diCl-C$_6$H$_3$ | 3 | 170 (EtOH) |

EXAMPLE 176

Hydroxyethyl 6-chloro-1-(2,4-dichlorophenyl)methyl-1,4-dihydro-2,4-dioxo-3(2H)-quinazolineacetate Into 10 ml of dried dimethylformamide were suspended 60 mg of sodium hydride (60%), and, to this was added dropwise a solution dissolved 500 mg of 6-chloro-1-(2,4-dichlorophenyl)methyl-1,4-dihydro-2,4-dioxo-3-(2H)-quinazolineacetic acid into 3 ml of dried dimethylformamide under stirring. After stirring the mixture for 30 minutes at room temperature, 160 mg of ethylene bromohydrin were added and the mixture was stirred for 4 hours at 110° C. After cooling by allowing to stand, the reaction mixture was poured into 200 ml of water and acidified with hydrochloric acid, which was extracted with ethyl acetate. After dried over anhydrous magnesium sulfate, solvent was distilled off and the residue was recrystallized from ethanol to obtain 300 mg of title compound. m.p. 167°–168° C.

Elemental analysis (%) as $C_{19}H_{15}Cl_3N_2O_5$ Calculated : C: 49.86 H: 3.30 N: 6.12. Observed : C: 49.88 H: 3.21 N: 6.16.

EXAMPLE 177

Following compound was synthesized through similar process to Example 176.

Pivaloyloxymethyl 6-chloro-1-(3,4-dichlorophenyl)-methyl-1,4-dihydro-2,4-dioxo-3(2H)-quinazolineacetate. m.p. 124°–126° C. (EtOH).

EXAMPLE 178

Ethyl 1-(2,4-dichlorophenyl)methyl-1,4-dihydro-2-oxo-4-thioxo-3(2H)-quinazolineacetate Into 100 ml of toluene was dissolved 3.80 g of ethyl 1-(2,4-dichlorophenyl)methyl-1,4-dihydro-2,4-dioxo-3(2H)-quinazolineacetate, and 5.70 g of Lawesson's reagent were added. After refluxed for 7 hours and 30 minutes, 1.90 g of Lawesson's reagent were further added and, after refluxed for 5 hours, solvent was distilled off. To the residue were added 10 ml of ethanol for washing, then it was further recrystallized from ethanol to obtain 2.80 g of title compound. m.p. 138°–139° C.

Elemental analysis as $C_{19}H_{16}Cl_2N_2O_3S$: Calculated: C: 53.91 H: 3.81 N: 6.62 Observed: C: 53.98 H: 3.76 N: 6.61

EXAMPLE 179–181

Following compounds were synthesized through similar process to Example 178.

EXAMPLE 179

Ethyl 1-(4-bromo-2-fluorophenyl)methyl-1,4-dihydro-2-oxo-4-thioxo-3(2H)-quinazolineacetate. m.p. 109°–110° C. (EtOH).

EXAMPLE 180

Ethyl 1-(4-bromo-2-fluorophenyl)methyl-6-chloro-1,4-dihydro-2-oxo-4-thioxo-3(2H)-quinazolineacetate. m.p. 89°–90° C. (EtOH).

EXAMPLE 181

Ethyl 1-(3,4-dichlorophenyl)methyl-1,4-dihydro-6-methyl-2-oxo-4-thioxo-3-(2H)-quinazolineacetate. m.p. 175.5°–177° C. (EtOH).

EXAMPLE 182

Ethyl 1-(3,4-dichlorophenyl)methyl-1,4-dihydro-2-oxo-4-thioxo-3(2H)-quinazolineacetate. m.p. 128°–129° C. (EtOH)

EXAMPLE 183

1-(2,4-Dichlorophenyl)methyl-1,4-dihydro-2-oxo-4-thioxo-3(2H)-quinazolineacetic acid.

Into 10 ml of acetic acid were dissolved 500 mg of ethyl 1-(2,4-dichlorophenyl)methyl-1,4-dihydro-2-oxo-4-thioxo-3(2H)-quinazolineacetate, and, after added 3 ml of concentrated hydrochloric acid and then 0.5 ml of concentrated sulfuric acid, the mixture was refluxed for 1 hour. After cooling by allowing to stand, the reaction mixture was poured into 200 ml of water and the deposits were collected by filtration. They were recrystallized from acetic acid to obtain 300 mg of title compound. m.p. 220°–221° C.

Elemental analysis as $C_{17}H_{12}Cl_2N_2O_3S$: Calculated : C: 51.66 H: 3.06 N: 7.09. Observed : C: 51.90 H: 3.05 N: 702.

EXAMPLE 184–186

Following compounds were synthesized through similar process to Example 183.

EXAMPLE 184

1-(4-Bromo-2-fluorophenyl)methyl-1,4-dihydro-2-oxo-4-thioxo-3(2H)-quinazolineacetic acid m.p. 269°–270.5° C. (EtOH).

EXAMPLE 185

1-(4-Bromo-2-fluorophenyl)methyl-6-chloro-1,4-dihydro-2-oxo-4-thioxo-3(2H)-quinazolineacetic acid m.p. 249.5°–250.5° C. (AcOEt).

EXAMPLE 186

1-(3,4-Dichlorophenyl)methyl-1,4-dihydro-2-oxo-4-thioxo-3(2H)-quinazolineacetic acid. m.p. 237°–238° C. ($CH_3CN$).

EXAMPLE 187

Ethyl 1-(2,4-dichlorophenyl)methyl-6-methoxy-1,4-dihydro-2,4-dioxo-3(2H)-quinazolineacetate Into 10 ml of dioxane were dissolved 5.2 g of ethyl (2-((2,4-dichlorophenyl)methyl)amino-5-methoxybenzoyl)aminoacetate and 6.2 g of N,N'-carbonyldiimidazole, and the solution was heated to 140° to 150° C. After distilled off dioxane, the mixture was further heated for 15 minutes at 140° C. After cooling, ethanol was added and the crystalline substances were collected by filtration. They were recrystallized from ethanol to obtain 2,8 g of title compound. m.p. 167°–168° C.

Elemental analysis (%) as $C_{20}H_{18}Cl_2N_2O_5$ Calculated : C: 54.94 H: 4.15 N: 6.41. Observed : CL 54.93 H: 4.11 N: 6.34.

EXAMPLE 188

Ethyl 1-(3,4-dichlorophenyl)methyl-1,4-dihydro-2,4-dioxo-6-imidazolylmethyl-3(2H)-quinazolineacetate In 30 ml of carbon tetrachloride were refluxed 3.5 g of ethyl 1-(3,4-dichlorophenyl)methyl-1,4-dihydro-2,4-dioxo-6-methyl-3(2H)-quinazolineacetate, 1.66 g of N-bromosuccinimide and calalytic amount of benzoyl peroxide for 2 hours. The insolubles were filtered off and the filtrate was concentrated. Ether was added to the residue for crystallization and the crystals thus obtained were recrystallized from acetonitrile to obtain 2.0 g of ethyl 6-bromomethyl-1 -(3,4-dichlorophenyl)-methyl-1,4-dihydro-2,4-dioxo-3(2H)-quinazolineacetate. m.p. 128°–129° C.

In 30 ml of dimethylformamide were stirred 1.90 g of above bromo compound, 0.28 g of imidazole and 0.53 g of potassium carbonate for 1.5 hours at 100° C. After cooling by allowing stand, the reaction mixture was poured into 500 ml of water and the crystals deposited were collected by filtration. They were purified by means of silica gel column chromatography (developing solvent, chloroform:methanol = 10:1) and recrystallized from acetonitrile to obtain 0.33 g of title compound. m.p. 201°–202° C.

Elemental analysis (%) as $C_{23}H_{20}Cl_2N_4O_4$: Calculated: CL 56.68 H: 4.14 N: 11.50 Observed: C: 56.57 H: 4.02 N: 11.26

EXAMPLE 189

1-(3,4-Dichlorophenyl)methyl-1,4-dihydro-2,4-dioxo-6-imidazolylmethyl-3(2H)-quinazolineacetic acid In 1.6 ml of 1N aqueous solution of sodium hydroxide and 20 ml of ethanol were refluxed 0.71 g of ethyl 1-(3,4-dichlorophenyl)methyl-1,4-dihydro-2,4-dioxo-6-imidazolylmethyl-3(2H)-quinazolineacetate for 1 hour. Ethanol was distilled off and the reaction mixture was neutralized with 3N hydrochloric acid. The crystals deposited were collected by filtration, washed with water and dried. They were recrystallized from acetic acid to obtain 0.50 g of title compound. m.p. 243°–244° C.

Elemental analysis (%) as $C_{21}H_{16}Cl_2N_4O_4 \cdot H_2O$: Calculated: C: 52.84 H: 3.80 N: 11.74. Observed: C: 52.55 H: 3.45 N: 11.45.

EXAMPLE 190

Ethyl 1,4-dihydro-2,4-dioxo-6-fluoro-7-imidazolyl-3(2H)-quinazolineacetate

A mixture of 20.0 g of ethyl (2-amino-4,5-difluorobenzoyl)aminoacetate, 25.1 g of N,N'-carbonyldiimidazole and 35 ml of dioxane was heated to 150° C. and, after distilled off dioxane, the mixture was heated for 1 hour. After cooling by allowing to stand, the crystals obtained were washed with methanol and recrystallized from dimethylformamide to obtain 13.8 g of title compound. m.p. 276°–278° C.

Elemental analysis (%) as $C_{15}H_{13}FN_4O_4$: Calculated: C: 54.22 H: 3.94 N: 16.86. Observed: C: 54.03 H: 3.98 N: 16.74.

EXAMPLE 191

Ethyl 1-(2,4-dichlorophenyl)methyl-1,4-dihydro-2,4-dioxo-6-fluoro-7-imidazolyl-3(2H)-quinazolineacetate Into 50 ml of dimethylformamide were dissolved 2.33 g of ethyl 1,4-dihydro-2,4-dioxo-6-fluoro-7-imidazolyl-3(2H)-quinazolineacetate, and, after added 0.97 g of potassium carbonate and 1.51 g of 2,4-dichlorobenzyl chloride, the mixture was stirred for 5 hours at 100° C. After cooling by allowing to stand, the reaction mixture was poured into 500 ml of water and the deposits were collected by filtration. They were recrystallized from ethanol to obtain 2.25 g of title compound. m.p. 192°–193° C.

Elemental analysis (%) as $C_{22}H_{17}Cl_2FN_4O_4$: Calculated: C: 53.78 H: 3.49 N: 11.40. Observed: C: 53.62 H: 3.54 N: 11.30.

EXAMPLE 192-193

Following compounds were synthesized through similar process to Example 191.

EXAMPLE 192

Ethyl 1,4-dihydro-2,4-dioxo-6-fluoro-7-imidazolyl-1-((4-trixluoromethyl)phenyl)methyl-3(2H)-quinazolineacetate. m.p. 132°–133° C. ($Et_2O$)

EXAMPLE 193

Ethyl 1-(3,4-dichlorophenyl)methyl-1,4-dihydro-2,4-dioxo-6-fluoro-7-imidazolyl-3(2H)-quinazolineacetate. m.p. 129°–130° C.

EXAMPLE 194

1-(2,4-Dichlorophenyl)methyl-1,4-dihydro-2,4-dioxo-6-fluoro-7-imidazolyl-3(2H)-quinazolineacetic acid Into 50 ml of ethanol were dissolved 2.0 g of ethyl 1-(2,4-dichlorophenyl)methyl-1,4-dihydro-2,4-dioxo-6-fluoro-7-imidazolyl-3(2H)-quinazolineacetate, and, after added 4.5 ml of 1N aqueous solution of sodium hydroxide, the mixture was refluxed for 1.5 hours. Ethanol was distilled off, water was added, pH was made to be 5 with 3N hydrochloric acid, and the deposits were collected by filtration. They were recrystallized from dioxane to obtain 930 mg of title compound. m.p. 188°–189° C.

Elemental analysis (%) as $C_{20}H_{13}Cl_2FN_4O_4$ Calculated: C: 51.85 H: 2.83 N: 12.10. Observed: C: 51.91 H: 2.91 N: 11.94.

EXAMPLE 195-196

Following compounds were synthesized through similar process to Example 194.

EXAMPLE 195

1,4-Dihydro-2,4-dioxo-6-fluoro-7-imidazolyl-1-((4-trifluoromethyl)phenyl)methyl-3(2H)-quinazolineacetic acid. m.p. 245°–246° C. (dioxane).

EXAMPLE 196

1-(3,4-Dichlorophenyl)methyl-1,4-dihydro-2,4-dioxo-6-fluoro-7-imidazolyl-3(2H)-quinazolineacetic acid. m.p. 251°–253° C. (dioxane).

UTILIZABILITY IN THE INDUSTRY

The novel quinazoline-3-alkanoic acid derivatives and their salts according to the invention have conspicuous hindering activity on aldose reductase and are useful drugs for the therapy and the prevention of complication of diabetes mellitus. Moreover, the compounds of the invention have excellent inhibitory effect on platelet aggregation and are also useful for the therapy of disorders of cerebral circulatory system, disease of arterial system, thrombosis, cardiac disease, ischemic fit and vascular disorders accompanied with diabetes mellitus.

EXPERIMENTAL EXAMPLE 1

Inhibitory effect on aldose reductase

Enzyme aldose reductase was partially purified from lens of rat and the inhibitory effect of the inventive compounds was determined using the method of Hyman et al (Hyman et al; J. Biol. Chem. 240, 877 (1965)). The $IC_{50}$ value (drug concentration for inhibiting 50% of enzyme activity) of the inventive compounds was $10^{-7}$ to $10^{-9}$M showing excellent inhibitory effect on aldose reductase.

EXPERIMENTAL EXAMPLE 2

Inhibitory effect on platelet aggregation

Using citric acid-excess platelet plasma of rabbit, the aggregation caused by arachidonic acid was measured with aggregometer. The $IC_{50}$ value (drug concentration for inhibiting 50% of platelet aggregation) was $10^{-5}$ to $10^{-7}$M showing excellent inhibitory effect on platelet aggregation.

We claim:

1. Quinazoline-3-alkanoic acid derivatives represented by a formula (I)

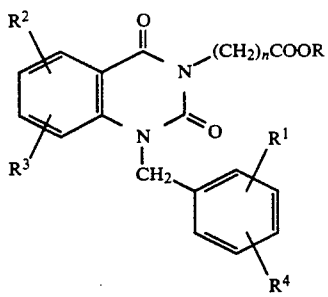

wherein R is hydrogen or alkyl group, $R^1$ and $R^4$ are identically or differently hydrogen or halogen, $R^2$ and $R^3$ are identically or differently hydrogen or halogen and n indicates an integer of 1 to 3; or their salts.

2. A pharmaceutical composition having an inhibitory effect on platelet aggregation comprising an effective amount of the compound of claim 1 in admixture with a pharmaceutically acceptable carrier or excipient.

3. A method of treating a subject in need of inhibition of platelet aggregation which comprises administering to the subject an effective amount of the compound of claim 1.

* * * * *